(12) United States Patent
Fabian et al.

(10) Patent No.: US 9,358,346 B2
(45) Date of Patent: Jun. 7, 2016

(54) NEEDLE ASSEMBLY FOR A PREFILLED SYRINGE SYSTEM

(75) Inventors: Arthur Fabian, Schaffhausen (CH); Stefan Beyeler, Schaffhausen (CH); Andreas Eberle, Ulm (DE); Jasminka Kovac, Diessenhofen (CH)

(73) Assignee: Cilag GMBH International, Landis & Gyrstrasse (CH)

( * ) Notice: Subject to any disclaimer, the term of this patent is extended or adjusted under 35 U.S.C. 154(b) by 0 days.

(21) Appl. No.: 13/601,024

(22) Filed: Aug. 31, 2012

(65) Prior Publication Data

US 2013/0261562 A1      Oct. 3, 2013

(51) Int. Cl.
*A61M 5/34* (2006.01)
*A61M 5/32* (2006.01)
*A61M 5/31* (2006.01)

(52) U.S. Cl.
CPC .............. *A61M 5/3202* (2013.01); *A61M 5/34* (2013.01); *A61M 2005/3109* (2013.01); *Y10T 29/49826* (2015.01); *Y10T 29/49904* (2015.01)

(58) Field of Classification Search
CPC ..... A61M 5/001; A61M 5/32; A61M 5/3202; A61M 5/3204; A61M 5/3205; A61M 2005/3206; A61M 5/321; A61M 5/3213; A61M 5/34; A61M 2005/3109
USPC .................................. 604/192, 197–199, 263
See application file for complete search history.

(56) References Cited

U.S. PATENT DOCUMENTS

| | | | |
|---|---|---|---|
| 1,845,036 A | 2/1932 | Busher | |
| 2,019,382 A | 10/1935 | Aronson | |
| 2,147,616 A | 2/1939 | Chaput | |
| 2,295,849 A | 9/1942 | Kayden | |
| 2,531,267 A | 11/1950 | Harisch | |
| 2,764,977 A | 10/1956 | Ferguson | |
| 2,828,742 A | 4/1958 | Ashkenaz | |
| 2,854,975 A | 10/1958 | Cohen | |
| 3,076,455 A | 2/1963 | McConnaughey et al. | |
| 3,131,692 A | 5/1964 | Love | |
| 3,320,955 A | 5/1967 | Sarnoff | |

(Continued)

FOREIGN PATENT DOCUMENTS

| | | |
|---|---|---|
| CH | 518102 A | 1/1972 |
| CN | 2059579 U | 7/1990 |

(Continued)

OTHER PUBLICATIONS

European Search Report dated Aug. 3, 2011; Application No. 11163779.9.

(Continued)

*Primary Examiner* — Quynh-Nhu H Vu

(57) ABSTRACT

A needle assembly (10; 210) for a prefilled injection syringe is described. A needle holder (12; 212) has a needle (14; 214) secured to it and is adapted to be secured to a syringe barrel of the injection syringe. A needle sheath (16; 216) has a distal end forming a releasable sterile seal with the needle holder (12; 212), and surrounds and shields the needle (14; 214). A needle seal (18; 218) surmounts the needle tip and is arranged at least in part in the proximal end of the needle sheath (16; 216) and closed off by a closure element (20; 220). A closure connection between the closure element (20; 220) and the needle sheath (16; 216) is configured as a non-releasable and sterile barrier (54; 254) produced by means of bonding or welding.

18 Claims, 3 Drawing Sheets

(56) References Cited

U.S. PATENT DOCUMENTS

| | | | |
|---|---|---|---|
| 3,329,146 | A | 7/1967 | Waldman |
| 3,543,603 | A | 12/1970 | Gley |
| 3,656,472 | A | 4/1972 | Ben Moura |
| 3,702,608 | A | 11/1972 | Tibbs |
| 3,742,948 | A | 7/1973 | Post et al. |
| 3,797,488 | A | 3/1974 | Hurschman et al. |
| 3,797,489 | A | 3/1974 | Sarnoff |
| 3,880,163 | A | 4/1975 | Ritterskamp |
| 3,976,069 | A | 8/1976 | Ong |
| 4,165,739 | A | 8/1979 | Doherty et al. |
| 4,180,070 | A | 12/1979 | Genese |
| 4,185,628 | A | 1/1980 | Kopfer |
| 4,194,505 | A | 3/1980 | Schmitz |
| 4,222,380 | A | 9/1980 | Terayama |
| 4,231,368 | A | 11/1980 | Becker |
| 4,236,516 | A | 12/1980 | Nilson |
| 4,299,238 | A | 11/1981 | Baidwan et al. |
| 4,333,459 | A | 6/1982 | Becker |
| 4,378,015 | A | 3/1983 | Wardlaw |
| 4,394,863 | A | 7/1983 | Bartner |
| 4,403,989 | A | 9/1983 | Christensen et al. |
| 4,407,283 | A | 10/1983 | Reynolds |
| 4,425,120 | A | 1/1984 | Sampson et al. |
| 4,430,082 | A | 2/1984 | Schwabacher |
| 4,507,118 | A * | 3/1985 | Dent .......................... 604/198 |
| 4,521,237 | A | 6/1985 | Logothetis |
| 4,561,856 | A | 12/1985 | Cochran et al. |
| 4,627,835 | A | 12/1986 | Fenton, Jr. |
| 4,636,201 | A | 1/1987 | Ambrose et al. |
| 4,639,250 | A | 1/1987 | Rycroft |
| 4,642,099 | A | 2/1987 | Phillips et al. |
| 4,676,530 | A | 6/1987 | Nordgren et al. |
| 4,695,274 | A * | 9/1987 | Fox .............................. 604/198 |
| 4,744,786 | A | 5/1988 | Hooven et al. |
| 4,787,891 | A | 11/1988 | Levin et al. |
| 4,874,383 | A | 10/1989 | McNaughton |
| 4,874,384 | A | 10/1989 | Nunez |
| 4,929,232 | A | 5/1990 | Sweeney et al. |
| 4,969,870 | A | 11/1990 | Kramer et al. |
| 4,988,339 | A | 1/1991 | Vadher |
| 5,009,646 | A | 4/1991 | Sudo et al. |
| 5,026,349 | A | 6/1991 | Schmitz et al. |
| 5,057,079 | A | 10/1991 | Tiemann et al. |
| 5,092,842 | A | 3/1992 | Bechtold et al. |
| 5,098,400 | A | 3/1992 | Crouse et al. |
| 5,112,119 | A | 5/1992 | Cooke et al. |
| 5,114,406 | A | 5/1992 | Gabriel et al. |
| 5,122,119 | A | 6/1992 | Lucas |
| 5,137,516 | A * | 8/1992 | Rand et al. .................... 604/136 |
| 5,141,496 | A | 8/1992 | Dalto et al. |
| 5,147,325 | A | 9/1992 | Mitchell et al. |
| 5,156,599 | A | 10/1992 | Ranford et al. |
| 5,176,643 | A | 1/1993 | Kramer et al. |
| 5,190,526 | A | 3/1993 | Murray et al. |
| 5,242,416 | A | 9/1993 | Hutson |
| 5,250,026 | A | 10/1993 | Ehrlich et al. |
| 5,250,037 | A | 10/1993 | Bitdinger |
| 5,263,933 | A | 11/1993 | Novacek et al. |
| 5,267,963 | A | 12/1993 | Bachynsky |
| 5,271,744 | A | 12/1993 | Kramer et al. |
| 5,295,965 | A | 3/1994 | Wilmot |
| 5,300,030 | A | 4/1994 | Crossman et al. |
| 5,312,364 | A | 5/1994 | Jacobs |
| 5,330,081 | A | 7/1994 | Davenport |
| 5,330,430 | A | 7/1994 | Sullivan |
| 5,356,395 | A | 10/1994 | Chen |
| 5,358,489 | A | 10/1994 | Wyrick |
| 5,364,369 | A | 11/1994 | Reynolds |
| 5,368,577 | A | 11/1994 | Teoh et al. |
| 5,372,586 | A | 12/1994 | Haber et al. |
| 5,391,151 | A | 2/1995 | Wilmot |
| 5,405,362 | A | 4/1995 | Kramer et al. |
| 5,411,488 | A | 5/1995 | Pagay et al. |
| 5,425,715 | A | 6/1995 | Dalling et al. |
| 5,451,210 | A | 9/1995 | Kramer et al. |
| 5,478,316 | A | 12/1995 | Bitdinger et al. |
| 5,480,387 | A | 1/1996 | Gabriel et al. |
| 5,487,732 | A | 1/1996 | Jeffrey |
| 5,489,256 | A | 2/1996 | Adair |
| 5,503,627 | A | 4/1996 | McKinnon et al. |
| 5,514,097 | A | 5/1996 | Knauer |
| 5,520,653 | A | 5/1996 | Reilly et al. |
| 5,540,660 | A | 7/1996 | Jenson et al. |
| 5,540,666 | A * | 7/1996 | Barta et al. .................... 604/192 |
| 5,540,709 | A | 7/1996 | Ramel et al. |
| 5,567,160 | A | 10/1996 | Massino |
| 5,569,191 | A | 10/1996 | Meyer |
| 5,569,192 | A | 10/1996 | van der Wal |
| 5,575,777 | A | 11/1996 | Cover et al. |
| 5,599,302 | A | 2/1997 | Lilley et al. |
| 5,599,309 | A | 2/1997 | Marshall et al. |
| 5,607,395 | A | 3/1997 | Ragsdale et al. |
| 5,609,577 | A | 3/1997 | Haber et al. |
| 5,609,584 | A | 3/1997 | Gettig et al. |
| 5,611,785 | A | 3/1997 | Mito et al. |
| 5,637,094 | A | 6/1997 | Stewart, Jr. et al. |
| 5,645,536 | A | 7/1997 | Whisson |
| 5,647,845 | A | 7/1997 | Haber et al. |
| 5,649,912 | A | 7/1997 | Peterson |
| 5,658,259 | A | 8/1997 | Pearson et al. |
| 5,665,071 | A | 9/1997 | Wyrick |
| 5,681,291 | A | 10/1997 | Galli |
| 5,697,908 | A | 12/1997 | Imbert |
| 5,702,367 | A | 12/1997 | Cover et al. |
| 5,704,911 | A | 1/1998 | Parsons et al. |
| 5,709,662 | A | 1/1998 | Olive et al. |
| 5,713,866 | A | 2/1998 | Wilmot |
| 5,748,316 | A | 5/1998 | Wakabayashi et al. |
| 5,779,668 | A | 7/1998 | Grabenkort |
| 5,779,677 | A | 7/1998 | Frezza |
| 5,807,334 | A | 9/1998 | Hodosh et al. |
| 5,817,058 | A | 10/1998 | Shaw |
| 5,827,262 | A | 10/1998 | Neftel et al. |
| 5,843,036 | A | 12/1998 | Olive et al. |
| 5,855,839 | A | 1/1999 | Brunel |
| 5,865,795 | A | 2/1999 | Schiff et al. |
| 5,865,804 | A | 2/1999 | Bachynsky |
| 5,868,711 | A | 2/1999 | Kramer et al. |
| 5,879,327 | A | 3/1999 | Moreau DeFarges et al. |
| 5,913,843 | A | 6/1999 | Jentzen |
| 5,928,205 | A | 7/1999 | Marshall |
| 5,954,738 | A | 9/1999 | LeVaughn et al. |
| 5,957,897 | A | 9/1999 | Jeffrey |
| 5,960,797 | A | 10/1999 | Kramer et al. |
| 5,989,229 | A * | 11/1999 | Chiappetta .................... 604/263 |
| 5,997,513 | A | 12/1999 | Smith et al. |
| 6,007,515 | A | 12/1999 | Epstein et al. |
| 6,015,438 | A | 1/2000 | Shaw |
| 6,017,330 | A | 1/2000 | Hitchins et al. |
| 6,036,675 | A | 3/2000 | Thorne et al. |
| 6,045,534 | A | 4/2000 | Jacobsen et al. |
| 6,068,614 | A | 5/2000 | Kimber et al. |
| 6,077,247 | A | 6/2000 | Marshall et al. |
| 6,083,197 | A | 7/2000 | Umbaugh |
| 6,086,562 | A | 7/2000 | Jacobsen et al. |
| 6,090,070 | A | 7/2000 | Hager et al. |
| 6,090,078 | A | 7/2000 | Erskine |
| 6,090,897 | A | 7/2000 | Akasaki et al. |
| 6,099,503 | A | 8/2000 | Stradella |
| 6,099,504 | A | 8/2000 | Gross |
| 6,123,684 | A | 9/2000 | Deboer et al. |
| 6,139,534 | A | 10/2000 | Niedospial, Jr. et al. |
| 6,159,161 | A | 12/2000 | Hodosh |
| 6,159,181 | A | 12/2000 | Crossman et al. |
| 6,159,184 | A | 12/2000 | Perez et al. |
| 6,162,199 | A | 12/2000 | Geringer |
| 6,171,276 | B1 | 1/2001 | Lippe et al. |
| 6,179,812 | B1 | 1/2001 | Botich et al. |
| 6,186,980 | B1 | 2/2001 | Brunel |
| 6,190,363 | B1 | 2/2001 | Gabbard et al. |
| 6,193,696 | B1 | 2/2001 | Jansen et al. |
| 6,203,530 | B1 | 3/2001 | Stewart |
| 6,209,738 | B1 | 4/2001 | Jansen et al. |
| 6,221,044 | B1 | 4/2001 | Grecco |

(56) References Cited

U.S. PATENT DOCUMENTS

| | | |
|---|---|---|
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie |
| 6,391,003 B1 | 5/2002 | Lesch |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B1 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 * | 11/2003 | Shemesh .................. 600/573 |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,409,141 B2 | 4/2013 | Johansen et al. |
| 8,491,530 B2 | 7/2013 | Maritan |
| 8,696,628 B2 | 4/2014 | Grunhut |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 * | 7/2002 | Larsen et al. .................. 604/187 |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |

(56) References Cited

U.S. PATENT DOCUMENTS

| | | |
|---|---|---|
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0063444 A1 | 3/2010 | Wikner |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0257193 A1 | 9/2014 | Bostrom et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |

(56) References Cited

FOREIGN PATENT DOCUMENTS

| | | |
|---|---|---|
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 2468330 A1 | 6/2012 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 A | 5/1920 |
| GB | 412054 A | 6/1934 |
| GB | 728248 A | 4/1955 |
| GB | 909898 A | 11/1962 |
| GB | 1263355 A | 2/1972 |
| GB | 1311937 A | 3/1973 |
| GB | 1514725 A | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| JP | 59-115053 A | 7/1984 |
| JP | 2-185261 A | 7/1990 |
| JP | 2-502971 T | 9/1990 |
| JP | H02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 A | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 A1 | 11/1988 |
| WO | WO 88/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 A1 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 A1 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |

(56) References Cited

FOREIGN PATENT DOCUMENTS

| | | |
|---|---|---|
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 A1 | 11/2003 |
| WO | WO 03/097133 A1 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | 2007/066152 A2 | 6/2007 |
| WO | WO 2007/066152 A | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 2010/023303 A1 | 3/2010 |

OTHER PUBLICATIONS

International Search Report dated Sep. 5, 2005; International Application No. PCT/GB2005/002117.
Singapore Search Report dated Mar. 15, 2012; Application No. SG 201007017-5.
International Search Report dated May 30, 2006; International Application No. PCT/GB2005/003725.
European Search Report dated Aug. 3, 2011; Application No. 11170040.7.
Australian Search Report dated Dec. 6, 2007; Application No. SG 200608164-0.
International Search Report dated Sep. 9, 2005; International Application No. PCT/GB2005/002126.
European Search Report dated Jul. 20, 2011; Application No. 11163762.5.
Austrian Search Report dated Nov. 11, 2008; Application No. 200608166-5.
International Search Report dated Sep. 5, 2005; International Application No. PCT/GB2005/002131.
International Search Report dated Sep. 9, 2005; International Application No. PCT/GB2005/002120.
Australian Search Report dated Feb. 26, 2008; Application No. SG 200608071-7.
International Search Report dated Sep. 5, 2005; International Application No. PCT/GB2005/002137.
European Search Report dated Apr. 23, 2007; Application No. 06077332.2.
European Search Report dated Feb. 28, 2011; Application No. 10179733.0.
European Search Report dated Mar. 4, 2011; Application No. 10179736.3.
International Search Report dated Sep. 6, 2005; International Application No. PCT/GB2005/002108.
European Search Report dated Jun. 16, 2011; Application No. 11160134.0.
Singapore Search Report dated Feb. 26, 2008; Application No. 200608070-9.
International Search Report dated Sep. 5, 2005; International Application No. PCT/GB2005/002105.
International Search Report dated Sep. 5, 2005; International Application No. PCT/GB2005/002116.
Australian Search Report dated Dec. 5, 2007; International Application No. SG-200608165-7.
International Search Report dated Sep. 5, 2005; International Application No. PCT/GB2005/002128.
International Search Report dated May 23, 2006; International Application No. PCT/GB2006/001017.
European Search Report dated Apr. 17, 2012; International Application No. 12157660.7.
European Search Report dated Apr. 17, 2012; International Application No. 12157661.5.
European Search Report Dated Oct. 16, 2012; European Application No. 12177505.0.
International Search Report dated May 29, 2006; International Application No. PCT/GB2006/001018.
International Search Report dated Jun. 2, 2006; International Application No. PCT/GB2006/001030.
European Search Report dated Aug. 4, 2011; Application No. 11169691.0.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.

(56) References Cited

OTHER PUBLICATIONS

European Search Report dated Feb. 1, 2006; Application No. 05255298.1.
International Search Report dated Feb. 27, 2007; International Application No. PCT/IB2006/002792.
Great Britain Search Report dated Sep. 22, 2006; Application No. GB0610860.9.
International Search Report dated Aug. 22, 2007; International Application No. PCT/GB2007/001992.
Great Britain Search Report dated Sep. 28, 2006; Application No. GB0610859.1.
International Search Report dated Sep. 4, 2007; International Application No. PCT/GB2007/002002.
International Search Report dated Aug. 22, 2007; International Application No. PCT/GB2007/001973.
International Search Report dated Feb. 26, 2008; International Application No. PCT/GB2007/004335.
Great Britain Search Report dated Sep. 29, 2006; Application No. GB0610856.7.
International Search Report dated Sep. 13, 2007; International Application No. PCT/GB2007/001999.
Great Britain Search Report dated Sep. 19, 2006; Application No. GB0610861.7.
International Search Report dated Aug. 28, 2007; International Application No. PCT/GB2007/001969.
Great Britain Search Report dated Nov. 12, 2007; Application No. GB0715460.2.
International Search Report dated Oct. 10, 2008; International Application No. PCT/GB2008/002578.
Great Britain Search Report dated Nov. 12, 2007; Application No. GB0715459.4.
International Search Report dated Oct. 14, 2008; International Application No. PCT/GB2008/002580.
Great Britain Search Report dated Nov. 12, 2007; Application No. GB0715461.0.
International Search Report dated Nov. 27, 2008; International Application No. PCT/GB2008/002579.
Great Britain Search Report dated Nov. 12, 2007; Application No. GB0715456.0.
International Search Report dated Oct. 10, 2008; International Application No. PCT/GB2008/002573.
Great Britain Search Report dated Nov. 8, 2007; Application No. GB0715457.8.
International Search Report dated Oct. 10, 2008; International Application No. PCT/GB2008/002583.
Great Britain Search Report dated Sep. 25, 2008; Application No. GB0811348.2.
International Search Report dated Sep. 30, 2009; International Application No. PCT/GB2009/001447.
European Search Report dated Oct. 15, 2013; Application No. 12182553.3.
Great Britain Search Report dated Sep. 25, 2008; Application No. GB0811346.6.
International Search Report dated Oct. 2, 2009; International Application No. PCT/GB2009/001448.
Great Britain Search Report dated Sep. 25, 2008; Application No. GB0811347.4.
International Search Report dated Oct. 5, 2009; International Application No. PCT/GB2009/001451.
Great Britain Search Report dated Sep. 25, 2008; Application No. GB0811345.8.
International Search Report dated Oct. 6, 2009; International Application No. PCT/GB2009/001453.
Great Britain Search Report dated Sep. 25, 2008; Application No. GB0811349.0.
International Search Report dated Oct. 5, 2009; International Application No. PCT/GB2009/001445.
Great Britain Search Report dated Sep. 25, 2008; Application No. GB0811343.3.
International Search Report dated Jan. 22, 2010; International Application No. PCT/GB2009/001446.
Great Britain Search Report dated Nov. 16, 2007; Application No. GB0716774.5.
International Search Report dated Jan. 12, 2008; International Application No. PCT/GB2008/002475.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.
International Search Report dated Sep. 9, 2014; International Application No. PCT/EP2014/062168.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Sep. 8, 2014; International Application No. PCT/EP2014/062162.
International Search Report dated Sep. 16, 2014; International Application No. PCT/EP2014/062160.
European Search Report dated Apr. 28, 2015; Application No. 15153304.9.
International Search Report dated Jan. 29, 2015; International Application No. PCT/EP2014/062167.
International Preliminary Report dated Dec. 15, 2015; International Application No. PCT/EP2014/062163.
International Preliminary Report dated Dec. 15, 2015; International Application No. PCT/EP2014/062166.

* cited by examiner

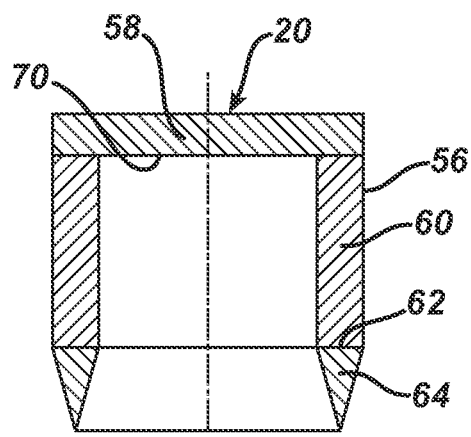
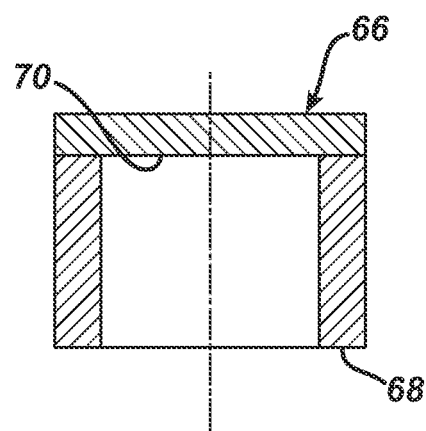
FIG. 3
FIG. 4
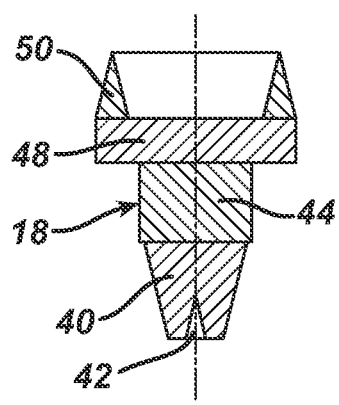
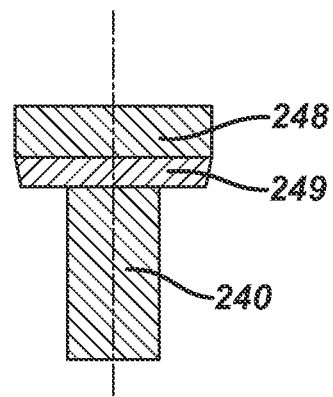
FIG. 5
FIG. 6

NEEDLE ASSEMBLY FOR A PREFILLED SYRINGE SYSTEM

The invention relates to a needle assembly for a prefilled injection syringe, especially but not exclusively of the type that is coated on the inside by means of baked siliconizing and sterilized in a heating tunnel at a temperature of up to 350° C., comprising: a needle holder with a needle secured thereto, the needle being securable to a syringe barrel of the injection syringe, a needle shielding sheath, the distal end of which fixedly sterile seals the needle holder, but releasably connected thereto and shieldingly surrounding the needle, a needle seal for mounting the needle tip arranged at least in part in the proximal end of the needle shielding sheath closed off by a closure element.

Systems of this kind are known and described inter alia in patents. Many of these known systems are, however, at a disadvantage or complicated in production and/or application.

Thus, a system is described in WO 94/22511 wherein a preassembled needle assembly with a bonded needle, needle seal as well as needle shield can be assembled e.g. in an aseptic environment to a siliconized and sterilized syringe barrel. A snap-action connector between end cap and cannula shield constitutes no microbiological shield for the needle in conjunction with the end contact face. Rendering the needle surface sterile is achieved by snap-action connection of cap and cannula shield, compressing the cannula shield of cap and cannula shield in sealing the resulting cavity surrounding the needle surface. Such a snap-action connector can be engineered releasable and thus represents a certain risk as regards rendering the needle surface sterile, as may be the case, e.g. when having become loose unnoticed during shipment or handling.

EP 0 240 787 describes a system for shielding parenteral needles involving a bonded needle, a needle seal and needle shield. There is no mention of how rendering the needle sterile is assured. Connecting the housing and needle hub is said to be achieved by axially staggered ribs which although achieving a certain secure location of the housing, fail to assure the necessary microbiological or sterile seal.

The invention is thus based on the object of improving a generic needle holder so that a sterile seal of the needle holder is assured in cost-saving production thereof so that maintaining the complete needle sterile in the time between sterilizing the needle assembly and the moment it is put to use is now reliably assured.

To achieve this object the invention is characterized by the closure connection between the closure element and the needle shielding sheath being configured as a non-releasable and sterile barrier produced by means of a bonding or welding technique.

Advantageous further embodiments of the invention read from the sub-claims.

Thus, the sterile barrier is preferably a closure connection produced by ultrasonic or laser welding.

Where a bonded connection finds application it is recommended to use non-toxic, acrylic-based adhesives for curing by means of UV light or at room temperature, such as e.g. adhesive type LOCTITE® 3011, Henkel Loctite Deutschland GmbH, 81925 Munich, epoxy resin by Barton Solvents Inc., Desmoines, USA.

Tests have shown that producing the closure element and the needle shielding sheath preferably of an amorphous thermoplastic, such as polycarbonate or polystyrene or a partly crystalline thermoplastic, such as polypropylene or polythene produces good results.

Particularly preferred is an embodiment in which the closure element is a cap with a cylindrical sleeve, and the needle shielding sheath is a tubular member, the proximal end of which is provided with a ring flange, the distal rim of the cap shell connecting the ring flange of the needle shielding sheath in forming a sterile barrier.

In this embodiment the ring flange of the needle shielding sheath may be provided at the outer edge of its proximal side to advantage with an annular face for securing the bottom rim of the cap shell.

It is furthermore advantageous when the distal rim of the cap shell comprises an interlocking profile, and the annular securing face of the ring flange of the needle shielding sheath comprises a receiving profile shaped to comply with the interlocking profile of the cap shell and in which the interlocking profile is inserted for positive and/or non-positive interlocking. The interlocking profile at the distal rim of the cap shell may also be shaped as an energy director where an ultrasonic weld with the needle shielding sheath is feasible.

Another aspect of the invention is characterized by a supporting collar jutting forwards from the proximal side of the ring flange of the needle shielding sheath radially within the outer annular securing face for the closure element.

To supplement this configuration the needle seal is provided at its proximal end preferably with a flange-type extension which is supported by the supporting collar of the needle shielding sheath. The distal side of the cover contacts the proximal end of the needle seal. In a further embodiment of the invention the proximal side of the flange-type extension of the needle seal is provided with a ring collar contacting the distal side of the head side of the closure element.

In this arrangement, preferably the supporting flange of the needle shielding sheath and the supporting collar may each comprise at the supporting flange of the needle shielding sheath a cylindrical centre hole whose bore corresponds to the bore of the cylindrical inner surface area of the needle shielding sheath.

This aspect can be modified in a second embodiment such that the inner surface area of the supporting collar of the needle shielding sheath is flared conically proximally and that the flange-type extension of the needle seal has a circumferential surface area which at least over a portion of its distal end matches the shape of the conical inner surface area of the supporting collar and is supported by this conical portion at the inner surface area of the supporting collar.

In addition, it is recommended that the distal end of the needle seal receiving the needle tip contains a central opening for the needle.

It is furthermore provided for that a longitudinal portion of the needle seal arranged distally of the flange-type extension extends by the supporting collar into the proximal end of the needle shielding sheath. In this arrangement the diameter of this distal longitudinal portion may be smaller or equal to the diameter of the inner space of the needle shielding sheath.

In addition it is particularly preferred that the needle shielding sheath is integrally connected at its distal end by a designed frangible connection to a proximal portion of the needle holder in thus making it possible to totally expose the needle ready for use after having destroyed just a single designed frangible connection.

It is recommended to produce the needle seal of a pharmaceutical rubber or a thermoplastic elastomer.

In conclusion, the needle should be preferably made of a stainless steel and either fixedly bonded in the needle holder coaxially to the barrel of the syringe or fixedly connected to the needle holder by a plastics potting. The needle holder itself may be made preferably of a thermoplastic, such as polycarbonate, polypropylene or polyamide.

From the above comments it will be appreciated that the needle assembly in accordance with the invention is excellently tamperproof on opening the prefilled injection syringe due to the sterile barrier between closure element and needle shielding sheath whilst assuring simple production and component assembly in producing the needle assembly as well as simple assembly of the needle assembly to a siliconized syringe barrel.

The preferred method of manufacturing the needle assembly includes securing a needle to a needle holder that is adapted to be secured to a syringe barrel of the injection syringe, releasably connecting the distal end of a needle sheath to the needle holder to form a sterile seal, and to surround and shield the needle, locating a needle seal on the needle tip and at least in part in the proximal end of the needle sheath, and closing off the proximal end of the needle seal with a closure element by forming a closure connection between the closure element and the needle sheath, configured as a non-releasable and sterile barrier, by means of bonding or welding.

In one particular manufacturing method, a first subassembly of the needle seal, closure element and needle sheath is formed, in which the needle seal is arranged at least in part in the proximal end of the needle sheath and the closure element closes off the proximal end of the needle seal, a second subassembly is formed by securing the needle to the needle holder, and the first and second subassemblies are offered up to one another so that the needle sheath releasably connects at its distal end to the needle holder to form a sterile seal, and surrounds and shields the needle, and the needle seal locates on the needle tip.

In an alternative manufacturing method, a first subassembly is formed by securing the needle to the needle holder, a second subassembly is formed by inserting the first subassembly into the needle sheath, a third subassembly is formed by mounting the needle seal onto needle tip and needle sheath of the second subassembly, and the needle assembly is completed by forming the closure connection between the closure element and the needle sheath of the third subassembly.

The invention will now be detailed by way of example embodiments with reference to the diagrammatic drawing in which:

FIG. 3 is a longitudinal centreline section, on a magnified scale, through a cover with an energy director prior to assembly, for a needle shielding sheath of the needle assembly as shown in FIG. 1 or 2;

FIG. 4 is a longitudinal centreline section, on a magnified scale, through a second modified embodiment of a cover for needle assembly;

FIG. 5 is a longitudinal centreline section, on a magnified scale, through a needle seal of the needle assembly as shown in FIG. 1; and FIG. 6 is a longitudinal centreline section, on a magnified scale, through a needle seal of the needle assembly as shown in FIG. 2.

Figure 1:
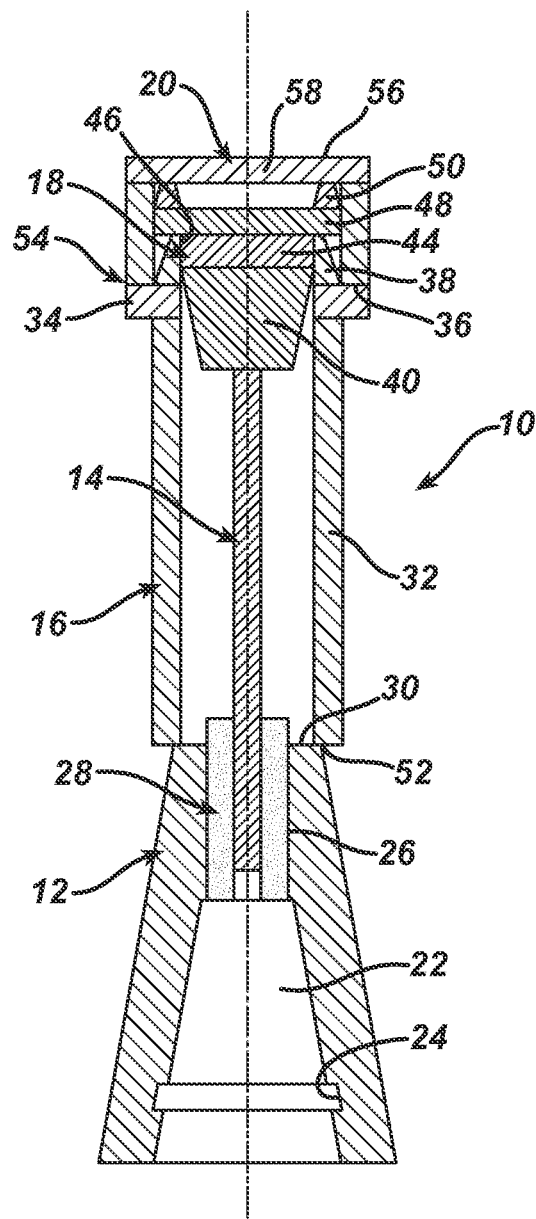
FIG. 1 is a longitudinal centreline section through a first embodiment of a needle assembly in accordance with the invention as it leaves production.

Referring now to FIG. 1 there is illustrated a needle assembly for a prefilled injection syringe made of glass or plastics, known as such and thus not shown, coated on the inside by means of baked siliconizing and sterilized in a heating tunnel at a temperature of up to 350° C. The needle assembly 10 is composed of a needle holder 12 and secured thereto a needle 14, a needle shielding sheath 16, a needle seal 18 and a closure element 20.

In detail, the needle holder 12 is tapered, featuring at its distal end a conical opening 22 provided with an annular groove 24 so that the needle holder 12 can be fitted to a moulded barrel with an annular bead of a prefilled injection syringe known as such and thus not shown, and secured thereto by snap-action connection. The conical opening 22 translates at its proximal end into a cylindrical bore 26 in which the needle 14 is coaxially secured by its distal end with the aid of an adhesive 28. Useful adhesives are non-toxic, acrylic-based adhesives for curing by means of UV light or at room temperature, such as e.g. adhesive type LOCTITE® 3011, Henkel Loctite Deutschland GmbH, 81925 Munich, epoxy resin by Barton Solvents Inc., Desmoines, USA.

Where necessary the needle 14 may also be secured by sleeve moulding it in the needle holder, whereby the same plastics material can be used for sleeve moulding the needle holder in an injection moulding technique as serving for production of the needle holder.

The needle 14 can be configured differing in length and is preferably made of a stainless steel of the type AISI 314 and is a cannula, the coaxially bore of which is exposed at the distal end. A proximal end of the needle holder 12 is an annular face 30 surrounding the bonded needle 14. The needle holder 12 is preferably made of a thermoplastic such as e.g. polycarbonate, polypropylene or polyamide.

The needle shielding sheath 16 mainly comprises a tubular longitudinal portion 32, the distal end of which is a secure and sterile seal connecting the outer edge of the annular face 30 of the needle shielding sheath 16 by a circumferential designed frangible connection 52, but which can be released manually by exerting a fracturing force.

The needle shielding sheath 16 extends coaxially to the needle holder 12 in surrounding the needle 14 with a full length consistent radial spacing. The outer diameter of the needle shielding sheath 16 is dimensioned only slightly larger than the diameter of the annular face 30 of the needle holder 12.

The needle shielding sheath 16 extends by its tubular longitudinal portion 32 beyond the tip (not shown in FIG. 1) of the needle, the proximal end of the tubular longitudinal portion 32 featuring a ring flange 34 surrounding an opening, the diameter of which roughly corresponds to the inner diameter of the needle shielding sheath 16.

The ring flange 34 extends outwards beyond the cylindrical outer side of the needle shielding sheath 16. The proximal end of the ring flange 34 features at its outer edge an annular securing face 36, an annular supporting collar 38 being arranged within this annular securing face 36. The inner diameter of this supporting collar 38 roughly corresponds to that of the needle shielding sheath 16 and ring flange 34 respectively. The needle shielding sheath 16 is preferably made of a partly crystalline thermoplastic, such as e.g. polypropylene or polythene.

Figure 2:
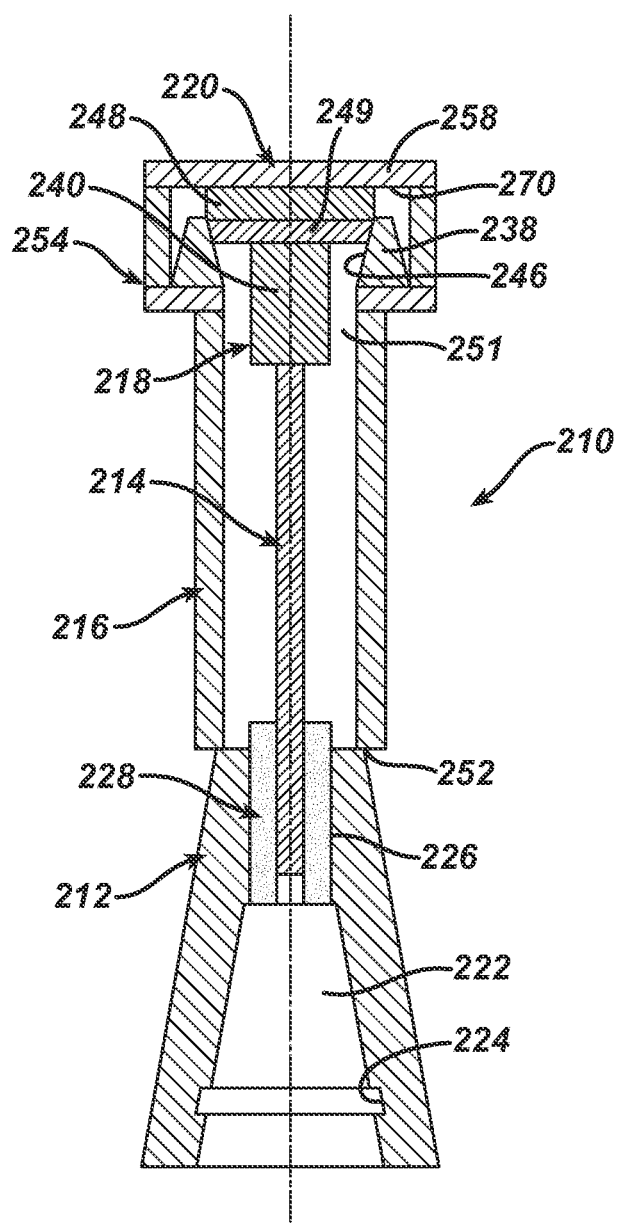
FIG. 2 is a longitudinal centreline section through a second embodiment of the invention as it leaves production.

In both embodiments of the needle assembly as shown in FIGS. 1 and 2 the needle seal 18 is made of an elastomeric material, such as pharmaceutical rubber or a thermoplastic elastomer, and serves to shieldingly receive a proximal end of the needle 14 comprising a bevelled needle tip, and which is arranged at least in part in the proximal end of the needle shielding sheath 16.

Referring now to the first embodiment as shown in FIG. 1 it is evident how the needle seal 18 comprises a moulding featuring a conical distal end 40 containing a centring opening 42 for the needle tip in extending over roughly half the length of the needle seal 18. The conical distal end 40 then translates into a short cylindrical longitudinal 10 portion 44 contacting a cylindrical inner surface area 46 of the supporting collar 38 of the needle shielding sheath 16. Before this short cylindrical longitudinal portion 44 the needle seal 18 is provided with a flange-type extension 48 supporting the needle seal 18 at the supporting collar 38 of the needle shielding sheath 16. A proximal end of the needle seal 18 is formed by an annular collar 50 protruding from an outer edge of the proximal end of the flange-type extension 48 of the needle seal 18.

Referring now to FIG. 5 there is illustrated a modified embodiment of the needle seal 18 in which merely a conical longitudinal portion 40 and a cylindrical longitudinal portion 44 located therebefore are dimensioned roughly the same in length. The annular collar 50 has a triangular cross-section, the apex of which is proximal.

The proximal end of the needle assembly 10 comprises the closure element 20 closing off the needle shielding sheath 16, this closure connection between the closure element 20 and needle shielding sheath 16 being configured as a sterile barrier 54.

Referring now to FIG. 1 again, there is illustrated how the closure element 20 is a cap 56 with a header plate 58, from the outer rim of which a cylindrical shell 60 extends distally. A distal rim 62 of the cylindrical shell 60 is connected to the securing face 36 of the ring flange 34 of the needle shielding sheath 16 in forming the sterile barrier 54. In this arrangement the closure element 20 clasps the portion of the needle seal 18 located before the supporting collar 38 as well as the supporting collar 38.

The sterile barrier 54 between the closure element 20 and the needle shielding sheath 16 comprises particularly to advantage a bonded or welded connection.

Where a bonded connection finds application it is recommended as mentioned above to use non-toxic acrylic-based adhesives for curing by means of UV light or at room temperature, such as e.g. adhesive type LOCTITE® 3011, Henkel Loctite Deutschland GmbH, 81925 Munich, epoxy resin by Barton Solvents Inc., Desmoines, USA.

In application of a welding technique preference is given to ultrasonic or laser welding techniques.

Where an ultrasonic weld is involved, the closure element 20, as shown in FIG. 3, is equipped at the distal rim 62 of its cap shell 60 preferably with an energy director 64 tapered distally into a triangular cross-section for faster, more effective welding of the distal rim 62 of the cap shell 60 to the securing face 36 at the outer edge of the ring flange 34 of the needle shielding sheath 16.

Referring now to FIG. 4 there is illustrated a cap 66 as a closure element 20, the cylindrical shell of which comprises a distal free end having a smooth annular surface area 68 extending perpendicular to the longitudinal centreline of the closure element 20. This embodiment is provided to close off the needle shielding sheath 16 by a bonded connection forming the sterile barrier 54.

It is recommended to produce the closure element 20 of an amorphous thermoplastic, such as polycarbonate or polystyrene or a partly crystalline thermoplastic, such as polypropylene or polythene.

Referring now to FIG. 1 again there is illustrated how the header plate 58 of the cap-type closure element 20 contacts a proximal end of the needle seal 18 by its distal side 70 (FIG. 3). In this arrangement of a first embodiment, the closure element 20 merely contacts the elastomeric annular collar 50 of the needle seal 18 in compressing it in part, so that the needle seal 18 with its flange-type extension 48 is pressed against the supporting collar 38 of the needle shielding sheath 16 when the needle shielding sheath 16 is closed off sterile by the closure element 20.

Referring now to FIG. 2 there is illustrated the needle assembly 210 in a second embodiment in accordance with the invention in which like or similar elements of the second embodiment are identified by like reference numerals of the first embodiment but prefixed by 2.

This needle assembly 210 differs from that of the first embodiment substantially in that the inner surface area of a supporting collar 238 of the needle shielding sheath 216 is flared conically proximally. As is evident from FIG. 2 and FIG. 6 a proximal flange-type extension 248 of the needle seal 218 comprises a circumferential surface area adapted at least in a partial portion of its distal end to the shape of the conical inner surface area 246 of the supporting collar 238 in being supported by this conical partial portion 246 on the conical inner surface area 246 of the supporting collar 238.

A portion 240 of the needle seal 218 extending distally of the flange-type extension 248 is formed cylindrical in interlocking the supporting collar 238 as well as the proximal end of the needle shielding sheath 216 in creating a free, annular space 251. The needle seal 218 in this case too is made of a pharmaceutical rubber or thermoplastic elastomer.

Missing furthermore from this second embodiment at the needle seal 218 is an annular collar protruding from the flange-type extension distally in the direction of the distal side of the header plate 258 of the closure element 220, resulting in the proximal side of the flange-type extension of the needle seal 218 directly contacting the distal side 270 of the header plate 258 of the closure element 220. The elastomeric material of the needle seal 218 is, however, in this second embodiment too, compressed by the closure element 220 when it is fixedly and non-releasable connected to the needle shielding sheath 216 to form a sterile barrier 254 with the needle shielding sheath 216.

The two main procedures in assembling the cap-type closure element and the needle shielding sheath are as follows:
1. joining the closure element by a welding or bonding technique, ensuring a good seal by the assurance of a full-length jointing seam (sterile barrier 54; 254),
2. positioning the flange of the needle seal when joining or assembling closure element and needle shielding sheath so that the resulting needle space is closed off microbiologically or sterile from the environment.

For the sake of completeness the steps in assembling the aforementioned needle assemblies are listed in the following in omitting the quality inspection steps:
1. picking and placing the needle holder;
2. picking and placing the needle and positioning the needle in the needle holder;
3. dispensing the adhesive and any follow-on steps as required, such as e.g. curing;
4. picking and placing the closure element
5. picking and placing the needle seal;
6. inserting the needle seal into the closure element;
7. picking and placing the needle shielding sheath
8. inserting the needle shielding sheath onto the closure element including the needle seal;
9. jointing and mounting method: securing the closure element on the needle shield sheath by means of welding or bonding and, if applicable, follow-on steps such as e.g. curing the adhesive in producing the sterile barrier;
10. inserting the needle and the needle holder into the needle shield sheath with the closure element and needle seal.

An alternative assembly method is as follows:
1. picking and placing the needle holder;

2. picking and placing the needle and positioning the needle in the needle holder;
3. dispensing the adhesive and any follow-on steps as required, such as e.g. curing;
4. picking and placing the needle sheath;
5. inserting the needle and the needle holder into the needle sheath;
6. picking and placing the needle seal and mounting onto needle tip and/or needle sheath;
7. picking and placing the closure element and mount onto needle shield sheath;
8. jointing and mounting method: securing the closure element on the needle shield sheath by means of welding or bonding and, if applicable, follow-on steps such as e.g. curing the adhesive in producing the sterile barrier.

It will thus be appreciated that the needle assembly in accordance with the invention ensures the needle remaining sterile during storage of the prefilled injection syringe in thus rendering it safely tamperproof. In addition, the needle assembly is simple to fit to a siliconized and sterilized syringe barrel on a mass production scale. All of the various component parts are simple to manufacture and assemble.

The invention claimed is:

1. A needle assembly (10; 210) for a prefilled injection syringe, comprising:
    a needle holder (12; 212) adapted to be secured to a syringe barrel of the injection syringe and a needle (14; 214) secured to the needle holder (12; 212);
    a needle sheath (16; 216) having a distal end and a proximal end, releasably connected at its distal end to the needle holder (12; 212) to form a sterile seal, and surrounding and shielding the needle (14; 214);
    a needle seal having a distal end and a proximal end (18; 218), located on the needle tip and arranged at least in part in the proximal end of the needle sheath (16; 216), said needle sheath (16; 216) being a tubular member (32;232); and
    a closure element (20; 220) that closes off the proximal end of the needle seal, said closure element (20;220) being a cap (56; 256) with a cylindrical shell (60;260) having a distal rim (62; 262);
    a closure connection between the closure element (20; 220) and the needle sheath (16; 216), configured as a permanently non-releasable and sterile barrier (54; 254) produced by means of bonding or welding; wherein
    the proximal end of the needle sheath (16; 216) is provided with a ring flange (34; 234) and the distal rim (62; 262) of said cap shell (60; 260) connects to said ring flange (34; 234) of said needle sheath (16; 216) to form the permanently non-releasable and sterile barrier (54; 254) produced by means of bonding or welding.

2. The needle assembly as set forth in claim 1, characterized in that said sterile barrier (54; 254) is produced by ultrasonic welding.

3. The needle assembly as set forth in claim 1, characterized in that said sterile barrier (54; 254) is produced by laser welding.

4. The needle assembly as set forth in claim 1, characterized by the use of non-toxic acrylic-based adhesives for curing by means of UV light or at room temperature for producing said sterile barrier (54; 254) by means of a bonding technique.

5. The needle assembly as set forth in claim 1, characterized in that said ring flange (34; 234) of said needle sheath (16; 216) is provided at the outer edge of its proximal side with an annular face (36; 236) for securing said distal rim (62; 262) of said cap shell (60; 260).

6. The needle assembly as set forth in claim 5, characterized by:
    a supporting collar (38; 238) jutting forwards from the proximal side of said ring flange (34; 234) of said needle sheath (16; 216) radially within said outer annular face (36; 236) for said closure element (20; 220),
    a flange-type extension (48; 248) of the upper end of said needle seal (18; 218) with which said needle seal (18; 218) is supported by said supporting collar (38; 238) of said needle sheath (16; 216) thereof, and
    the distal side (70) of said closure element (20; 220) contacting a proximal end of said needle seal (18; 218).

7. The needle assembly as set forth in claim 6, characterized in that the proximal end of said flange-type extension (48; 248) of said needle seal (18; 218) is provided with a ring collar (50; 250) contacting the distal side (70; 270) of said header plate (58; 258) of said closure element (20; 220).

8. The needle assembly as set forth in claim 6, characterized in that said ring flange (34; 234) of said needle sheath (16) and said supporting collar (38) each comprise at said ring flange (34) or said needle sheath (16; 216) a cylindrical inner surface area (46) whose bore corresponds to the bore of said cylindrical inner surface area of said needle sheath (16).

9. The needle assembly as set forth in claim 6, characterized in that said inner surface area (246) of said supporting collar (238) of said needle sheath (216) is flared conically proximally and that said flange-type extension (248) of said needle seal (218) has a circumferential surface area which at least over a portion (249) of its distal end matches the shape of said conical inner surface area (246) of said supporting collar (238) and is supported by this conical partial portion (248) at said inner surface area (246) or said supporting collar (238).

10. The needle assembly as set forth in claim 1, characterized in that the distal end of said needle seal (18) receiving said needle tip contains a central opening (42) for said needle (14).

11. The needle assembly as set forth in claim 6, characterized in that a portion (40; 240) of said needle seal (18; 218) arranged distally of said flange-type extension (48; 248) extends into said supporting collar (38; 238) into the proximal end of said needle sheath (16; 216), and comprises a diameter substantially equal to that of the inner space of said needle sheath (16; 216).

12. The needle assembly as set forth in any of the claims 7 to 9, characterized in that said needle sheath (16; 216) is integrally connected at its distal end by a designed frangible connection (52; 252) to a proximal portion of said needle holder.

13. The needle assembly as set forth in claim 1, characterized in that said closure element (20; 220) and said needle sheath (16; 216) are made of an amorphous or partly crystalline thermoplastic, such as polypropylene or polythene.

14. The needle assembly as set forth in claim 1, characterized in that said needle seal (18; 218) is made of a pharmaceutical rubber or a thermoplastic elastomer.

15. The needle assembly as set forth in claim 1, characterized in that said needle (14; 214) is made of a stainless steel.

16. The needle assembly as set forth in claim 1, characterized in that said needle (14; 214) is fixedly bonded in said needle holder (12; 212) coaxially to said needle sheath (16; 216).

17. The needle assembly as set forth in claim 1, characterized in that said needle (14; 214) is fixedly connected to said needle holder (12; 212) by a plastics potting.

18. The needle assembly as set forth in claim 1, characterized in that said needle holder (12; 212) is made of a thermoplastic such as polycarbonate, polypropylene or polyamide.

\* \* \* \* \*